United States Patent
Erdogan et al.

(10) Patent No.: US 11,928,821 B2
(45) Date of Patent: Mar. 12, 2024

(54) EVALUATION METHOD FOR HAIR TRANSPLANT PROCESS USING IMAGE PROCESSING AND ROBOTIC TECHNOLOGIES AND SYSTEM THEREOF

(71) Applicant: KEBOT BILISIM TEKNOLOJILERI SANAYI VE TICARET ANONIM SIRKETI, Istanbul (TR)

(72) Inventors: Koray Erdogan, Istanbul (TR); Oguzhan Urhan, Kocaeli (TR)

(73) Assignee: KEBOT BILISIM TEKNOLOJILERI SANAYI VE TICARET ANONIM SIRKETI, Istanbul (TR)

( * ) Notice: Subject to any disclaimer, the term of this patent is extended or adjusted under 35 U.S.C. 154(b) by 251 days.

(21) Appl. No.: 17/046,308

(22) PCT Filed: Mar. 26, 2019

(86) PCT No.: PCT/TR2019/050192
§ 371 (c)(1),
(2) Date: Oct. 9, 2020

(87) PCT Pub. No.: WO2020/013778
PCT Pub. Date: Jan. 16, 2020

(65) Prior Publication Data
US 2021/0082117 A1    Mar. 18, 2021

(30) Foreign Application Priority Data
Apr. 26, 2018    (TR) ................. 2018/05930

(51) Int. Cl.
*G06T 7/00*    (2017.01)
*A61B 34/10*    (2016.01)

(52) U.S. Cl.
CPC ............ *G06T 7/0016* (2013.01); *A61B 34/10* (2016.02); *A61B 2034/104* (2016.02);
(Continued)

(58) Field of Classification Search
CPC ......... G06T 7/0016; G06T 2207/10028; G06T 2207/10048; G06T 2207/30088; A61B 34/10; A61B 2034/104
(Continued)

(56) References Cited

U.S. PATENT DOCUMENTS

2002/0103500 A1    8/2002   Gildenberg
2012/0116417 A1    5/2012   Bodduluri et al.
(Continued)

FOREIGN PATENT DOCUMENTS

CN    103702607 A   *   4/2014  ............. A61B 34/30
CN    203605907 U   *   5/2014
(Continued)

*Primary Examiner* — Wednel Cadeau
(74) *Attorney, Agent, or Firm* — Bayramoglu Law Offices LLC

(57) ABSTRACT

A method and system based on the image processing technology and robotic technologies are used for planning and evaluating the processes of the hair transplant operations. This method allows a rapid detection of the follicle, the hair number in each follicle and the hair thickness on the images obtained by the scanning of the scalp of the patient before the operation through the image processing technology. Considering these data, "Coverage Value" calculation is automatically carried out; maximum hair number to be harvested in each area is automatically analyzed and calculated. As a result, more reliable and healthy results relative to the present operations are obtained for evaluating the whole operational process through the systematic data, and a system facilitating the method is applied.

17 Claims, 5 Drawing Sheets

(52) U.S. Cl.
CPC ............... *G06T 2207/10028* (2013.01); *G06T 2207/10048* (2013.01); *G06T 2207/30088* (2013.01)

(58) Field of Classification Search
USPC ......................................................... 382/133
See application file for complete search history.

(56) References Cited

U.S. PATENT DOCUMENTS

| | | | |
|---|---|---|---|
| 2014/0278321 A1* | 9/2014 | Zhang | G16H 50/50 |
| | | | 703/11 |
| 2016/0042512 A1 | 2/2016 | Zhang et al. | |
| 2016/0148435 A1 | 5/2016 | Li et al. | |

FOREIGN PATENT DOCUMENTS

| | | | | |
|---|---|---|---|---|
| CN | 105844648 A | | 8/2016 | |
| ES | 2656954 T3 | * | 3/2018 | ............. A45D 26/00 |
| KR | 2009030341 A | * | 3/2009 | ......... G06K 9/00127 |
| MX | 2017004743 A | | 7/2017 | |
| WO | 2017040615 A1 | | 3/2017 | |
| WO | WO-2019152522 A1 | * | 8/2019 | ............. A61K 35/33 |

* cited by examiner

EVALUATION METHOD FOR HAIR TRANSPLANT PROCESS USING IMAGE PROCESSING AND ROBOTIC TECHNOLOGIES AND SYSTEM THEREOF

CROSS REFERENCE TO THE RELATED APPLICATIONS

This application is the national phase entry of International Application No. PCT/TR2019/050192, filed on Mar. 26, 2019, which is based upon and claims priority to Turkish Patent Application No. 2018/05930, filed on Apr. 26, 2018, the entire contents of which are incorporated herein by reference.

TECHNICAL FIELD

The present invention relates to a novel method and system which is based on the image processing technology and robotic technologies which are used for planning and evaluating the processes of the hair transplant operations. The invention relates to a method for planning the hair transplant operations being a common treatment in the medical field, so as to obtain more reliable and healthy results relative to the present operations and for evaluating the whole operational process through the systematic data, and a system facilitating said method to be applied.

BACKGROUND

Currently, many people suffer from hair loss and baldness problems which are particularly due to the genetic and stress factors, and they resort to hair transplant operations in order to prevent such losses and to have their previous appearances they prefer. The metabolic changes of women and men, nutrition disorders, excess weight and weight loss, drug uses, and the results of the serious treatment processes are considered among the factors of the hair losses, in addition to the genetic and stress-based factors. In order to prevent such problems, people generally try certain products such as herbal and chemical drugs, cures, shampoos and lotions, serums, but unfortunately they are not able to be eliminate the problems by such methods which are not proved to be reliable and permanent. Today, instead of the products which cannot provide accurate results, those who suffer from said problems prefer the hair transplant operation, the results of which are medically proven and totally permanent, owing to the developing technology.

The hair transplant is a process of transferring the strong hairs which are genetically not to be lost from a hairy area to a hairless area in the sterile operating room environment by various methods. In the earlier years when these operations started to be executed, it used to be performed for particularly male-type hair losses (baldness, sparse hair, etc.); today it is used for the treatments of the patients who suffer from hair losses.

The hairs (named as graft) taken from the person who suffer from said problem are selected from the areas genetically coded not to be lost. This area is genetically resistant to balding, from which the hairs are gathered for said operations, and on which the hairs are densely present is referred to as "donor site". The grafts taken from said donor sites are placed into the balding sites by the professionals in the field and the transplantation process is completed. Because said grafts are resistant to balding, they do not lose their features even if it is applied to any balding area and they protect their genetic features in the areas where they transplanted. The hair loss cases of a person relates to the genetic code of the follicle, instead of the scalp or a definite area. As well as hair, also the transplantation may be carried out in the eyelash, eyebrow, side whiskers, and mustache areas.

Hair losses also may derive from the decreased blood values, particularly zinc and iron deficiencies. Before the hair transplant operation, these values should be checked, if there is a deficiency, the required treatment processes for normalizing these values should be carried out, and then a decision should be made for the hair transplant operation. In the current treatments, the hair transplant process is mainly planned according to the doctor's experiences. This may cause failed practices because of the wrong decisions. For instance, there may be baldness in the area from which follicles will be harvested because of harvesting excessive or disproportional follicles from said area.

Before the operation, the hairy areas of a patient's head are scanned through a robotic system comprising cameras by means of the method and system of the invention which are developed upon the problems mentioned above and the applied treatments. After this scanning process, various features of the person's hair are determined, and the number of the hairs and the area from which said hairs will be harvested for the hair transplant are determined according to a predetermined analysis system. After the hair transplant operation, the harvested follicle number and the transplanted follicle number are determined by a subsequent scanning. Thus, the quantitative evaluation of the operational success is enabled.

In the prior art, the number of the hair follicles to be harvested and the area from which they will be harvested is determined according to the doctor's experience. The only objective criterion to be used for this is the calculation of "Coverage Value" which was developed by Dr. Koray ERDOĞAN. This criterion basically uses the hear number in a definite area (e.g. 1 cm$^2$) and the numerical analysis of their thicknesses in order to determine the effect of the hairs to cover the scalp. By said approach, the maximum follicle harvest (donor capacity) to be performed in said area is determined in order to prevent balding in the area from which the follicles will be harvested (donor site).

While this approach provides significant advantages in practice, it is a quite difficult process to be applied. The photos of the definite areas of the patient's head are taken before the operation, a very time-consuming counting process is realized by an operator on these photos, and estimation is carried out about the hair density on the head. Also, the hair sample (graft) taken from the related area of the patient and its thickness is measured by a caliper, the "Coverage Value" is calculated over different areas of the head, and from which areas the follicles will be harvested is determined according to this analysis.

In the prior art, apart from the analysis method described above, there is no criterion to evaluate the success of the operation after a hair transplant operation. The patients do not know how many hairs are harvested and how many of them are transplanted successfully.

In the prior art, there are many patents and designs for conventional hair transplant operations, methods, and systems. However, there are no patent found for a product with a similar system structure which is capable of planning the success of the hair transplant operation in detail and analyzing the results, by the similar method using the image processing and robotic technologies.

In the U.S. Patent No. US2016042512A1, a novel method for rapidly processing the image of the related area by means of the robotic systems in a hair transplant operation or in any surgical operation. It is a result of the analysis that an output created by overlapping various images of the related area may be used as an input for another operation. However, in said patent, a method and system are not disclosed which is based on the image processing technology and robotic technologies which are used for planning and evaluating the processes of the hair transplant operations.

In the International patent no. WO2017040615A1, a method for creating a head simulation by placing a two-dimensional (2D) head image onto a three dimensional (3D) model and estimating the outputs of the subsequent operations on this program. However, a method and system is not disclosed which is based on the image processing technology and robotic technologies which are used for planning and evaluating the processes of the hair transplant operations.

In the U.S. Patent no. US2016148435, a system is disclosed which facilitates the calculation of the operations to be realized in a real plane by 3 dimensional models. However, in said patent, a method and system are not disclosed which is based on the image processing technology and robotic technologies which are used for planning and evaluating the processes of the hair transplant operations.

In the Chinese patent no CN105844648, the measurement systems are disclosed which are based on the camera used for evaluating the hair quality and the image processing technology. Hair care advices and recipes are formed based on the data obtained from said system. However, in said patent, a method and system are not disclosed which is based on the image processing technology and robotic technologies which are used for planning and evaluating the processes of the hair transplant operations.

In the Mexican patent no. MX2017004743A, a system used for the analysis on the scalp through the infrared lights. The images obtained by a video-camera are transferred to an analysis unit, and the analysis and the consultation for the hair is carried out. However, in said patent, a method and system are not disclosed which is based on the image processing technology and robotic technologies which are used for planning and evaluating the processes of the hair transplant operations.

In said patents, the operations performed by image processing and this technology, but an invention which discloses a method and system being based on the image processing technology used for planning the process of the hair transplant operations with similar features and evaluating the results thereof is not described.

SUMMARY

The invention aims to develop a method which is capable of planning the process and operational success of the hair transplant operation in detail and analyzing the results thereof and to realize said planning and analysis activities through the created system by using the image processing and robotic technologies in the hair transplant operations. The invention comprises a method constituted to obtain more reliable and accurate results for the hair transplant operations being a common practice in the medical field through a different system from the conventional operations, and a system allowing applying said method.

It has already been mentioned that in the prior art, the photos of the definite areas of the patient's head are taken before the operation, a manual counting process taking a long time is realized by the visual ability of an operator on these photos, and an estimation is carried out about the hair density on the head. While this approach provides significant advantages in practice, it is a quite difficult and time-consuming process to perform the operation in such manner. There are some significant deficiencies of said approach. First of them is that the photos of only a restricted area of the head may be taken and then the counting of the determined follicles is performed in the "Coverage Value" calculation. The result of this calculation is assumed to be the same over the whole area in said application. However, there may be hair structures with different features within the same area. Also, another disadvantage of said method that the measurement carried out by a caliper results in the measurement faults of said method. As mentioned above, it is one of the disadvantages that the thickness of the hair taken as a sample may not represent the all of the hairs.

The most significant advantage of the evaluation method of the hair transplant process and the system of the method disclosed in the invention is that it allows planning the whole process before the hair transplant treatment and numerically evaluating the success of the operation after the hair transplant treatment by means of the developed image processing technology and robotic technologies.

Another advantage of the evaluation method of the hair transplant process and the system of the method disclosed in the invention is that it allows a rapid detection of the follicle, the hair number in each follicle and the hair thickness on the images obtained by the scanning of the scalp of the patient before the operation through the image processing technology. Considering these data, "Coverage Value" calculation is automatically carried out; maximum hair number to be harvested in each area is automatically analyzed and calculated.

Another advantage of the evaluation method of the hair transplant process and the system of the method disclosed in the invention is that the patient's head is scanned by a robotic system comprising cameras after the operation and upon this scanning, the follicle number to be harvested from the patient's head, the number of those which can be transplanted and the success rate of the whole process may be automatically detected.

In the hair transplant evaluation method of the invention and the system of said method, the drawings will be helpful for better understanding the image processing- and robotic technologies-based system used for planning and evaluating the system.

Figure 1:
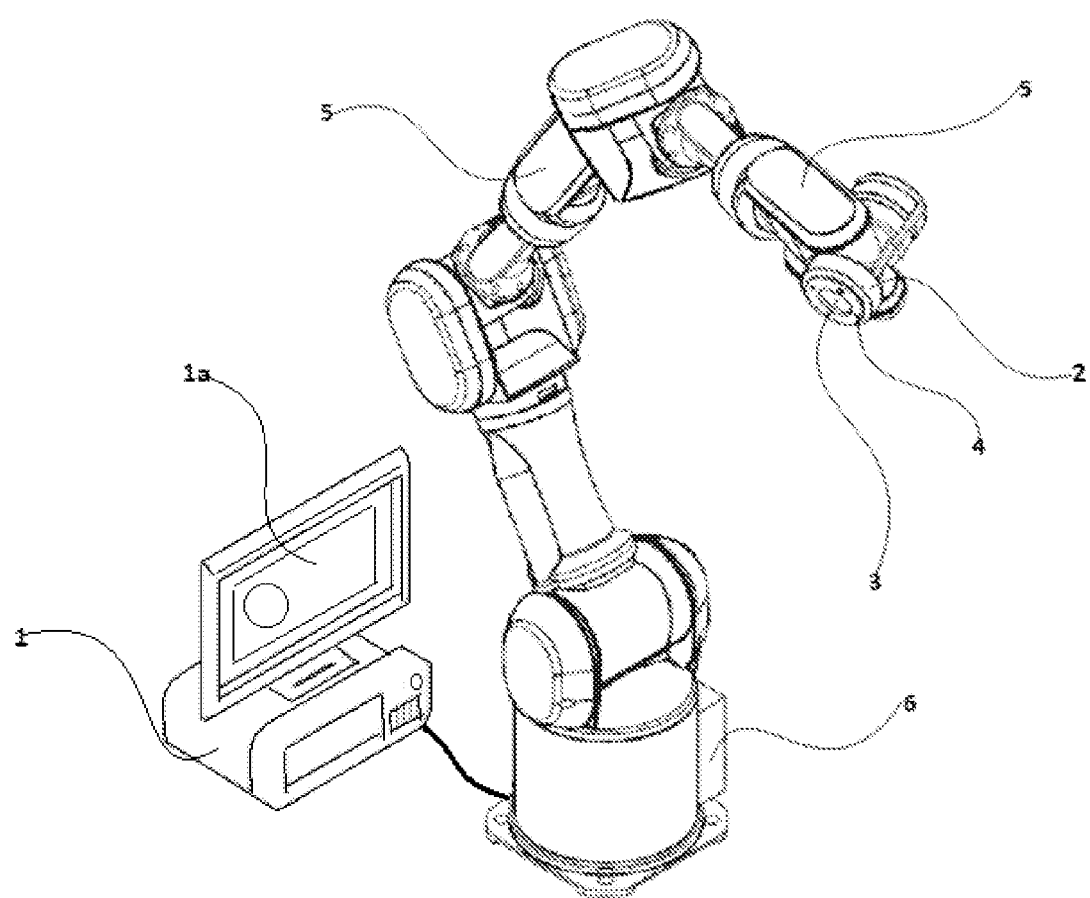
FIG. 1 is a representative view showing the components of the system of the invention.

STAGE NAMES, REFERENCE NUMERALS OF THE SECTIONS AND PARTS TO SERVE FOR DESCRIBING THE INVENTION

1—Operational unit
1a—User interface-screen
2—Camera
3—Lenses
4—Lighting element
5—Robotic systems
6—Robot controller
7—Donor site
7a—Hair graft
Method Stages;
110: Initial stage
120: Image-taking stage before the operation
130: Calculation stage
140: Transplant stage
150: Image-taking stage after the operation
160: Calculation and reporting stage

DETAILED DESCRIPTION OF THE EMBODIMENTS

The invention comprises developing a method using the image processing technology in cooperation with the robotic technologies in order to plan and evaluate the process in the hair transplant operations and realizing said evaluation method by a novel technological system. The invention comprises a method constituted to obtain more reliable and accurate results for the hair transplant operations being a common practice in the medical field through a different manner from the conventional operations and being based on the analysis of the situation before and after the treatment and the comparison therebetween, and also the image processing technologies and robotic systems allowing applying said operations.

Figure 2:
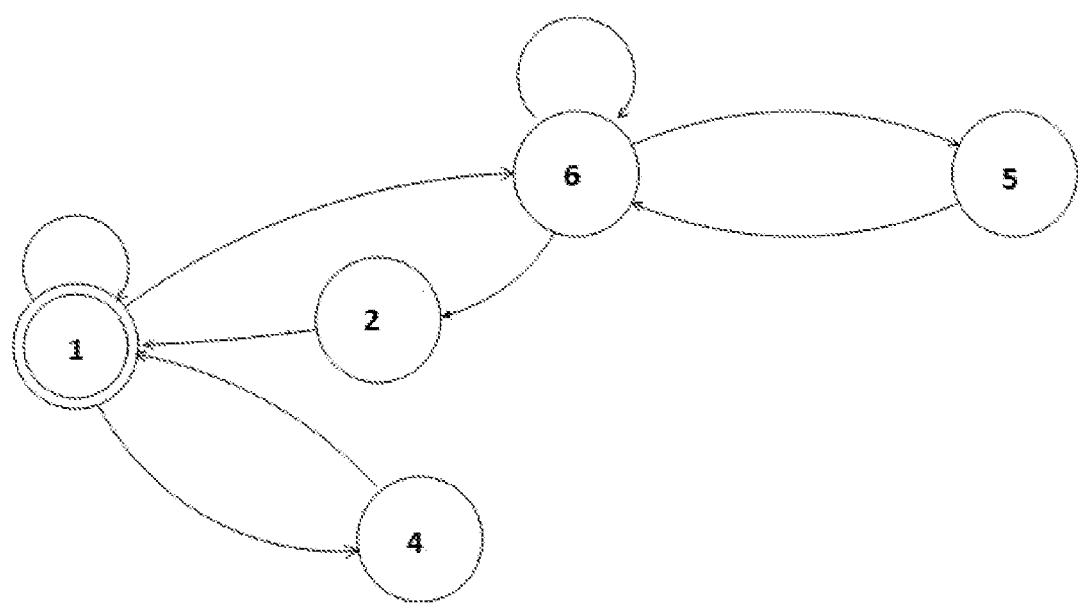
FIG. 2 is a schematic view showing the components of the system of the invention and the connection therebetween.
Figure 3A:
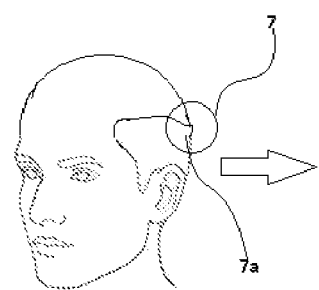
FIG. 3A is a representative view showing the donor site and hair graft determined on the head before the operation by using the system of the invention.
Figure 3B:
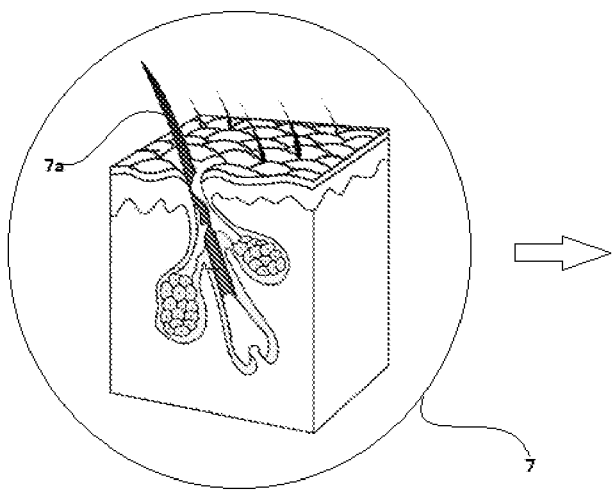
FIG. 3B is a detailed view showing the hair graft to be harvested from the donor site determined by using the system of the invention and the structure thereof.
Figure 3C:
FIG. 3C is a representative view showing the results of the treatment on the head after the operation by using the system of the invention.
Figure 4A:
FIG. 4A is a schematic view showing the area, the image of which is taken by the system of the invention and on which the transplant will be performed.
Figure 4B:
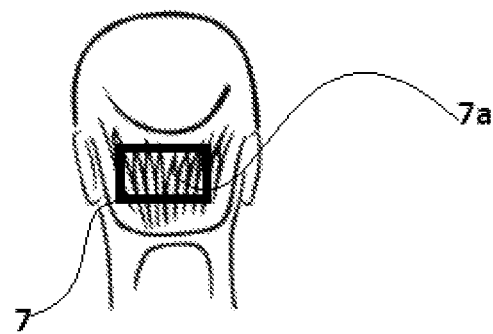
FIG. 4B is a schematic view showing the position of the donor site determined by the system of the invention on the head.
Figure 5:
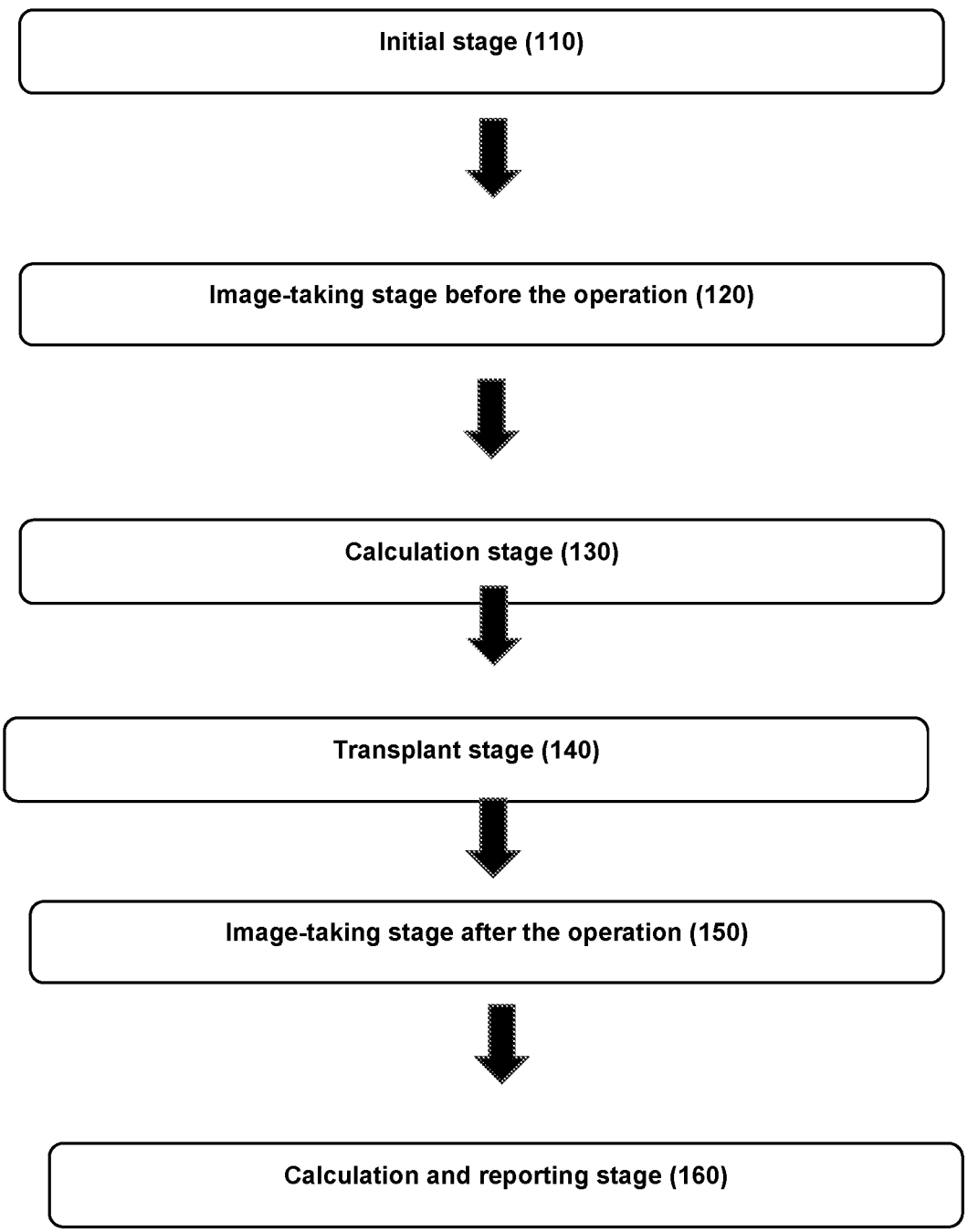
FIG. 5 is a flow chart showing the process steps in the system of the invention.

FIG. 1 is a representative view showing the components of the system of the invention. FIG. 2 is a schematic view showing the components of the system of the invention. FIG. 3A is a representative view showing the donor site determined by use of the system of the invention, the hair graft harvested therefrom, and the situation of the head before the hair transplant. FIG. 3B is a detailed view showing the hair graft to be harvested from the donor site and the structure thereof. FIG. 3C is a representative view showing the situation of the head after the hair transplant. FIG. 4A and FIG. 4B are the representative view showing the area on which the hair transplant is performed and the donor site. FIG. 5 is a flow chart showing the process steps in the system of the invention.

The system comprised by the method of the invention generally comprises an operational unit (1), the camera (2) systems in connection with said operational unit (1) and the robotic systems (5) controlled by the operational unit (1), also the lighting elements (4) being capable of emitting light in different wavelengths in order to capture the images recorded by the camera (2) systems more effectively, and the robot controller (6) enabling the motion of the whole system.

In the operational unit (1) section arranged on the system of the invention, a computer element which is capable of working alone or in an embedded manner, for example stationary/portable computers or embedded cards carrying MCU (Micro Controller), DSP (Digital Signal Processor), FPGA (Field Programmable Gate Array), or GPU (Graphic Processing Unit) may be used. In said system, the cameras (2) detecting the image, being visible, detecting the infrared (IR—Infrared Radiation) lights, having depth sensibility (Stereo or Time-of-flight etc.) and the lenses (3) being appropriate for the function of said camera (2) systems are used. The telecentric or bi-telecentric lenses (3) may be used in said system as an alternative to the conventional lenses especially for thickness measurement and counting.

The robotic system (5) moving the lighting elements (4) and the cameras (2) used in the system of the invention are responsible for taking the cameras (2) to the preferred position. The positions of the cameras (2) are calculated by the operational unit (1) through the program located therein. The required commands are transferred to the robotic system (5) by the robot controller (6) after said calculation process. After taking the images obtained by said cameras (2), counting, analysis, evaluation, and reporting steps are performed by the operational unit (1) again. Therefore, a separate calculation unit may be used in the system.

In the system of the invention, the cameras (2) capable of measuring the depth and/or calculation scan the head of the person to be treated with hair transplant by means of the robotic system (5) and a three-dimensional (3D) model of the head is outlined in a digital environment. In order to screen the head in detail over the outlined three-dimensional model, a route is determined to follow, the robotic system (5) is moved along said route, and it takes the images of a standard visible area and/or definite areas of the head by means of the IR cameras (2). Said images are taken during the subsequent shots such that the images will be overlapping. The overlap degree of said images taken is calculated by using the image processing techniques. The data of said overlap degree are used to eliminate the counting in the overlapping areas both while creating a combined image from the images taken separately and realizing the counting processes on the separate images.

The follicle number on various areas of the head, hair number in each follicle, and the areas of the marked fields on the head are calculated over the images taken before the operation. Coverage Value calculation is carried out for each area by using these data and the total donor capacity of the patient, the maximum follicle, i.e. hair graft (7a) number to be harvested from the donor sites (7) are determined. These calculations are carried out by the image processing algorithms functioning on the operational unit (1). While these calculations may be carried out in parallel with the image-taking process, it may also be made after the whole image taking process.

After the operation, the number of the follicles harvested from the head, i.e. Hair graft (7a) is determined from the new image taken by the camera (2) being capable of measuring/calculating the predetermined route or depth, along the route to be determined. These calculations are carried out by the image processing algorithms functioning on the operational unit (1). While these calculations may be carried out in parallel with the image-taking process, it may also be made after the whole image taking process. The quantitative evaluation of the operation is possible by means of these calculations.

The method having the image processing technology and the robotic technologies used for the hair transplant planning and evaluation operations, considering it as a process flow, mainly comprises the following stages:
Initial stage (110)
Image-taking stage before the operation (120)
Calculation stage (130)

Transplant stage (140)

Image-taking stage after the operation (150)

Calculation and reporting stage (160)

Initial stage (110): At the initial stage, the person is firstly positioned in front of the developed robotic system (5) in the determined area and position in order to enable the planning of the whole process and then carrying out the analyses. The operator activates the related command through the user interface (1a) in order to actuate the system and the operational unit (1) sends the required commands to the robot controller (6) and switches the robotic system (5) to the initial position.

After the first stage, the operational unit (1) sends the required command to the cameras (2) and enable the cameras (2) to be ready for taking images. The operator may control the system directly through the operational unit (1) or through a user interface (screen) (1a) connected to the operational unit (1).

Image-taking stage before the operation (120): This stage consists of two separate process steps. In the first step, a three-dimensional image is created on the interface by moving a camera (2) which is capable of calculating the depth around the head of the person by means of the robotic system (5). After this scanning process, the route is planned by the operational unit (1) over said three-dimensional data. In the second step, the visible/IR cameras (2) are brought to the appropriate points around the head through the robotic system (5) over the planned route and the images are taken which have partial overlaps between each other.

Calculation stage (130): In this stage, the follicle number, the hair number in each follicle and the hair thickness are calculated through the image processing technology by using the images taken at the previous stage. During this process, the fields of various areas marked on the head are also calculated. After these basic calculations, the Coverage Value calculation is carried out for the whole head and for the certain donor sites (7) on the head and the regional donor capacity is calculated.

Transplant stage (140): The results of the analysis is evaluated which has carried out by using the method of the invention and the system of said method at the previous stage and the hair grafts (7a) taken from the donor sites (7) by the doctors are transplanted to the areas where there are hair sparseness.

Image-taking stage after the operation (150): The image-taking stage after the operation is performed in a similar way to the image-taking step before the operation (120). Also the previous three dimensional model information of the person may be used without doing an additional three dimensional scanning for the same person or the images are taken through a pre-calculated route or through a route created after a new scanning.

Calculation and reporting stage (160): At this stage, the number of follicles taken from the donor sites (7) and the transplanted follicle number is determined by the image processing techniques over the images taken at the previous stage. Thus, the operational unit (1) calculates how many hairs are taken from an area of the head and how many of them can be transplanted.

These calculations are then reported so as to inform the doctor and the person who had the operation.

INDUSTRIAL APPLICABILITY OF THE INVENTION

The technology and the technical system used in the present invention is developed to count and analyze considerably small objects on a big non-planar area by the image processing techniques. In various counting processes in the industry, there are "pick-and-place" applications intended for detecting and changing the location of the objects with greater sizes. The invention presented in this patent will enable these processes to be more effectively carried out for the objects with relatively smaller sizes and provide new technological developments.

What is claimed is:

1. A system for planning and evaluating a process of a hair transplant operation, comprising:
    an operational unit;
    a user interface-screen element facilitating a control of the operational unit;
    at least one camera detecting an image in the system;
    at least one lighting element capable of emitting light with stable or different wavelengths; and
    a robot controller providing mobility for a robotic system, wherein the robotic system provides movement for the lighting element(s) and the camera(s);
    wherein the system is based on an image processing technology and a robotic technology; and
    wherein the operational unit is configured to automatically calculate data comprising a follicle number, a number of hairs at each follicle, and a hair thickness based on the images taken, and to use the data to automatically calculate a Coverage Value for the whole area of the head and for each area covering the scalp that is used to determine a donor capacity of a head region and prevent balding of the donor site and calculate;
    wherein the system is configured to detect a follicle number harvested from a donor site and a transplanted follicle number over three-dimensional images by the image processing technology after the hair transplant operation, determine a number of hair taken from the donor site and a number of transplanted hair by the operational unit after the hair transplant operation, evaluate after the hair transplant operation an overall success of the hair transplant operation by the operational unit, and report the overall success to inform a doctor and a person having the hair transplant operation.

2. The system according to claim 1, further comprising telecentric or bi-telecentric lenses in accordance with a function of the at least one camera.

3. The system according to claim 1, wherein the operational unit comprises one of a computer element capable of functioning separately, a computer element in an embedded position, stationary-portable computers, or embedded cards carrying MCU (Micro Controller), DSP (Digital Signal Processor), FPGA (Field Programmable Gate Array), or GPU (Graphic Processing Unit).

4. The system according to claim 2, wherein the operational unit comprises one of MCU (Micro Controller), DSP (Digital Signal Processor), FPGA (Field Programmable Gate Array), or GPU (Graphic Processing Unit).

5. A method for planning and evaluating a process of a hair transplant operation, wherein the method is based on an image processing technology and a robotic technology, and the method comprises:
    an initial stage;
    an image-taking stage before the hair transplant operation;
    a calculation stage;
    a transplant stage;
    an image-taking stage after the hair transplant operation; and a calculation and reporting stage;

wherein the calculation stage comprises steps of calculating data comprising a follicle number, a number of hairs at each follicle, and a hair thickness, and further comprises calculating, based on said data, a Coverage Value for the whole head and for each area covering the scalp that is used to determine a donor capacity of a head region and prevent balding of the donor site;

wherein the calculation and reporting stage comprising:

detecting a follicle number harvested from a donor site and a transplanted follicle number over three-dimensional images by image processing technologies after the hair transplant operation, determining a number of hair taken from the donor site and a number of transplanted hair by an operational unit after the hair transplant operation, evaluating after the hair transplant operation an overall success of the hair transplant operation by the operational unit, and reporting the overall success to inform a doctor and a person having the hair transplant operation.

6. The method according to claim 5, wherein the initial stage comprises steps of positioning a person to be hair transplanted in a determined area for the hair transplant operation to be performed by using a robotic system, activating a command through a user interface by an operator and then switching the robotic system to a suitable position for initiating a scanning process of a head of the person via sending required commands to a robot controller by an operational unit.

7. The method according to claim 5, wherein the image-taking stage before the hair transplant operation comprises steps of moving a camera capable of calculating a depth through a robotic system and creating a three-dimensional image of a head of a person.

8. The method according to claim 5, wherein the image-taking stage before the hair transplant operation comprises steps of performing a planned route using three dimensional data obtained through an operational unit, bringing visible and/or IR cameras to appropriate points around a head by a help of a robotic system along the planned route, and taking images having partial overlaps of each other.

9. The method according to claim 5, wherein the steps of calculating the follicle number, the hair number at each follicle, and the hair thickness are performed by using an image processing technology over images taken at the image-taking stage before the hair transplant operation, and the calculation stage further comprises calculating fields of various areas marked on a head.

10. The method according to claim 5, wherein the transplant stage comprises transplanting hair grafts harvested from donor sites to parts with sparse hair on a head in a sterile environment by evaluating analysis results obtained in the calculation stage.

11. The method according to claim 5, wherein the image taking stage after the hair transplant operation comprises a step of taking images of a head using a pre-calculated route or a route created after a new three dimensional scanning, wherein the image taking stage after the hair transplant operation is performed by using previous three-dimensional model information of the head in a similar way to the image-taking stage before the hair transplant operation, with or without performing an additional three-dimensional scanning for the head.

12. The method according to claim 5, wherein the initial stage comprises steps of sending required commands to cameras by an operational unit on a robotic system and preparing the cameras to take images.

13. The method according to claim 5, wherein the transplant stage comprises transplanting hair grafts harvested from donor sites to parts with sparse hair on the head in a sterile environment by evaluating analysis results obtained in the calculation stage.

14. The method according to claim 6, wherein the initial stage further comprises steps of sending the required commands to cameras by the operational unit on the robotic system and preparing the cameras to take images.

15. The method according to claim 7, wherein the image-taking stage before the hair transplant operation comprises steps of performing a planned route using three-dimensional data obtained through an operational unit, bringing visible and/or IR cameras to appropriate points around the head by a help of the robotic system along the planned route, and taking images having partial overlaps of each other.

16. The method according to claim 8, wherein the steps of calculating the follicle number, the hair number at each follicle, and the hair thickness are performed by using an image processing technology over images taken at the image-taking stage before the hair transplant operation, and the calculation stage further comprises calculating fields of various areas marked on a head.

17. The method according to claim 14, wherein the image-taking stage before the hair transplant operation comprises steps of moving a camera capable of calculating a depth through the robotic system and creating a three-dimensional image of the head of the person.

* * * * *